United States Patent
Lan

(10) Patent No.: US 12,197,084 B2
(45) Date of Patent: Jan. 14, 2025

(54) ORGANIC COMPOUND, POLYMER PREPARED BY THE ORGANIC COMPOUND, AND DISPLAY PANEL CONTAINING THE POLYMER

(71) Applicant: GUANGZHOU CHINA STAR OPTOELECTRONICS SEMICONDUCTOR DISPLAY TECHNOLOGY CO., LTD., Guangdong (CN)

(72) Inventor: Song Lan, Guangdong (CN)

(73) Assignee: GUANGZHOU CHINA STAR OPTOELECTRONICS SEMICONDUCTOR DISPLAY TECHNOLOGY CO., LTD., Guangzhou (CN)

( * ) Notice: Subject to any disclaimer, the term of this patent is extended or adjusted under 35 U.S.C. 154(b) by 0 days.

(21) Appl. No.: 18/175,554

(22) Filed: Feb. 28, 2023

(65) Prior Publication Data
US 2024/0255807 A1    Aug. 1, 2024

(30) Foreign Application Priority Data
Dec. 30, 2022    (CN) .......................... 202211739865.0

(51) Int. Cl.
G02F 1/1337    (2006.01)
C07D 213/73    (2006.01)
(Continued)

(52) U.S. Cl.
CPC ...... *G02F 1/133711* (2013.01); *C07D 213/73* (2013.01); *C07D 471/04* (2013.01); *C08G 69/40* (2013.01)

(58) Field of Classification Search
CPC ................ C07D 213/73; C07D 221/10; C07D 471/04; C08G 69/40; C08G 73/1085;
(Continued)

(56) References Cited

FOREIGN PATENT DOCUMENTS

CN    105038817 A  * 11/2015
CN    115558103 A  *  1/2023    ......... C08G 73/1007
(Continued)

*Primary Examiner* — Sophie Hon
*Assistant Examiner* — Sow-Fun Hon
(74) *Attorney, Agent, or Firm* — PV IP PC; Wei Te Chung

(57) ABSTRACT

The disclosure provides an organic compound, a polymer prepared by the organic compound, and a display panel containing the polymer. The organic compound is represented by formula (1) or formula (2). $X_1$, $X_2$, $X_3$, and $X_4$ are each independently selected from $-CR_2$ and N, $X_1$ and $X_2$ are not $CR_2$ at the same time, and $X_3$ and $X_4$ are not $CR_2$ at the same time, $R_1$ is independently selected from a single bond, a substituted or unsubstituted $C_6$-$C_{14}$ aromatic group, and a substituted or unsubstituted $C_5$-$C_{13}$ heteroaromatic group, and $R_2$ is independently selected from $-H$ or $NH_2$.

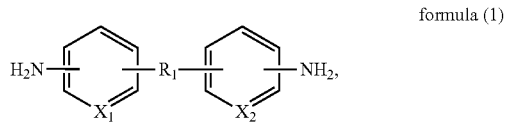

formula (1)

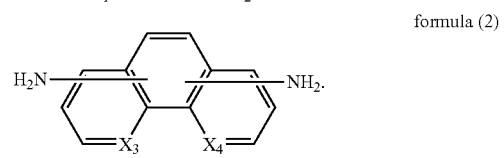

formula (2)

13 Claims, 2 Drawing Sheets

(51) Int. Cl.
*C07D 471/04* (2006.01)
*C08G 69/40* (2006.01)

(58) Field of Classification Search
CPC ........... C08G 73/1042; G02F 1/133711; G02F 1/133723; C09K 2323/025; C09K 2323/027
See application file for complete search history.

(56) References Cited

FOREIGN PATENT DOCUMENTS

| | | | | |
|---|---|---|---|---|
| GB | 2353795 A | * | 3/2001 | ........... C07D 471/14 |
| JP | 6183616 B2 | * | 8/2017 | ............. C08G 73/10 |

* cited by examiner

ORGANIC COMPOUND, POLYMER PREPARED BY THE ORGANIC COMPOUND, AND DISPLAY PANEL CONTAINING THE POLYMER

TECHNICAL FIELD

The disclosure relates to the technical field of display, in particular to an organic compound, a polymer prepared by the organic compound, and a display panel containing the polymer.

BACKGROUND

In current technologies, liquid crystal displays (LCDs) are widely used in the technical field of display. Liquid crystal molecules in the LCDs can deflect orderly under voltage driving of electrodes, so as to achieve a luminous function. Realization of the luminous function requires that the liquid crystal molecules have certain pretilt angles generated from alignment films. However, existing alignment films have a problem that charges are accumulated and difficult to be released due to high density of ions (such as ions from liquid crystal layers), which leads to disorder of liquid crystal orientation and residual shadow of display panels, thus making it difficult to improve quality of the display panels.

Therefore, an organic compound, a polymer, and a display panel are urgently needed to solve the above-mentioned technical problem.

SUMMARY

The disclosure provides an organic compound, a polymer prepared by the organic compound, and a display panel containing the polymer, which can alleviate a technical problem of residual shadow caused by difficulty in releasing accumulated charges in existing alignment films.

The disclosure provides the organic compound represented by formula (1) or formula (2):

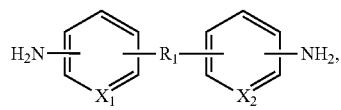

formula (1)

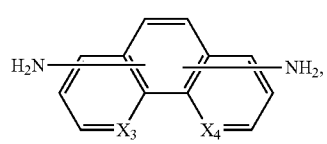

formula (2)

wherein $X_1$, $X_2$, $X_3$, and $X_4$ are each independently selected from $CR_2$ and N, $X_1$ and $X_2$ are not $CR_2$ at the same time, and $X_3$ and $X_4$ are not $CR_2$ at the same time;

$R_1$ is independently selected from a single bond, a substituted or unsubstituted $C_6$-$C_{14}$ aromatic group, and a substituted or unsubstituted $C_5$-$C_{13}$ heteroaromatic group; and $R_2$ is independently selected from —H or $NH_2$.

Preferably, the organic compound is represented by formula (3) or formula (4):

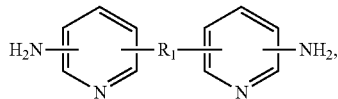

formula (3)

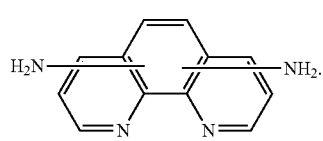

formula (4)

Preferably, the organic compound is selected from following compounds:

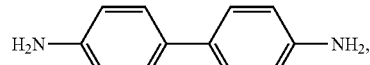

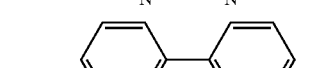

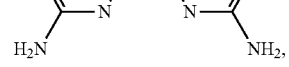

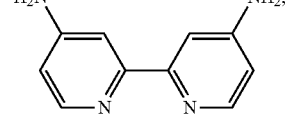

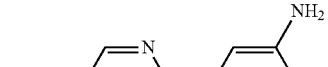

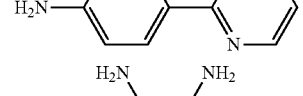

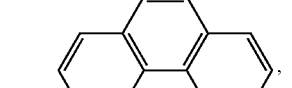

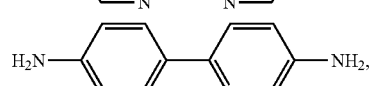

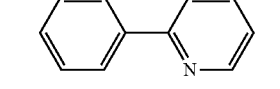

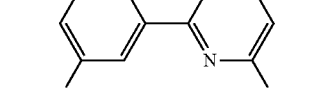

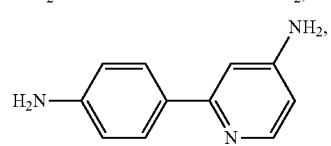

-continued

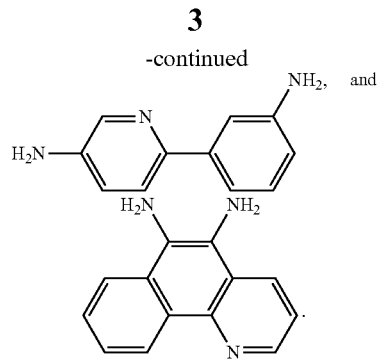

The disclosure further provides the polymer obtained by a reaction of a first type of raw material and a second type of raw material;
wherein the first type of raw material includes the above-mentioned organic compound.

Preferably, the first type of raw material includes a first monomer and a second monomer, the first monomer is the organic compound as above, the second monomer is diamine, and the second monomer the same or different from the first monomer; and the second type of raw material includes a third monomer and a fourth monomer, the third monomer and the fourth monomer are tetracarboxylic dianhydride, and the fourth monomer the same or different from the third monomer.

Preferably, the second monomer is represented by

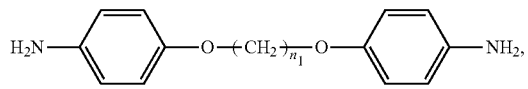

wherein $n_1$ is an integer selected from 2, 3, and 4.

Preferably, the third monomer and the fourth monomer are selected from following compounds:

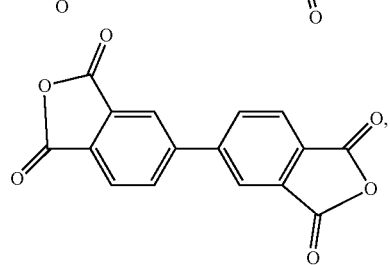

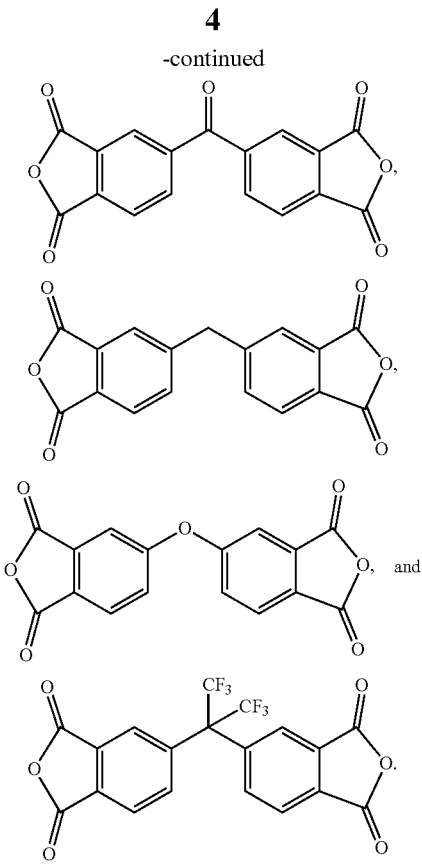

Preferably, the polymer is represented by formula (5):

formula (5)

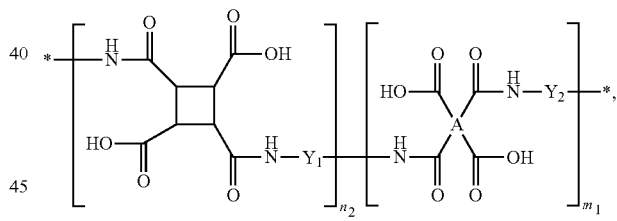

a ratio of $n_2$ to $m_1$ ranges from (2:8) to (5:5);
$Y_1$ is represented by

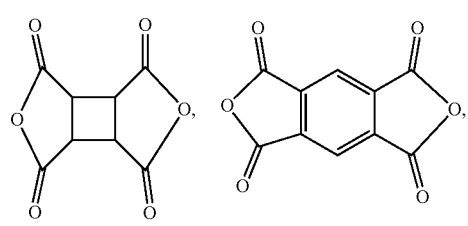

wherein $n_1$ is an integer selected from 2, 3, and 4;
A is selected from following compounds:

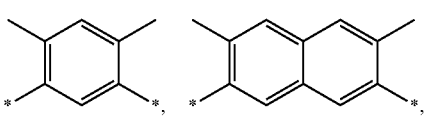

-continued
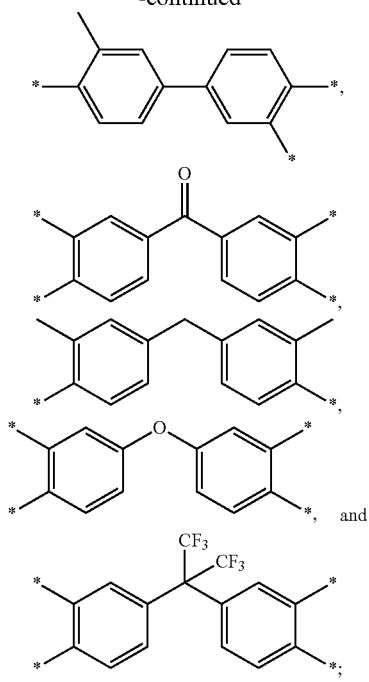
and
$Y_2$ is represented by formula (6) or formula (7):
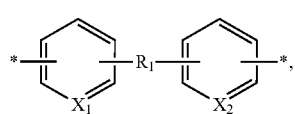
formula (6)
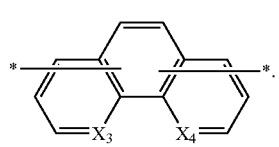
formula (7)
Preferably, the polymer is selected from following compounds:
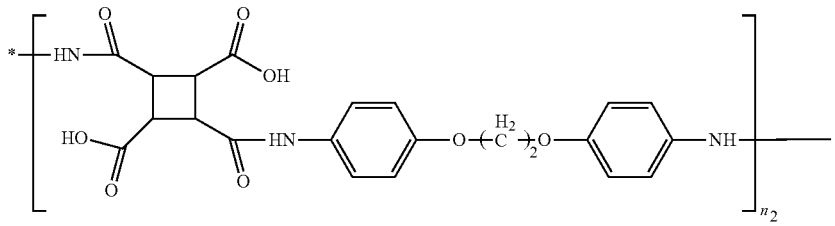
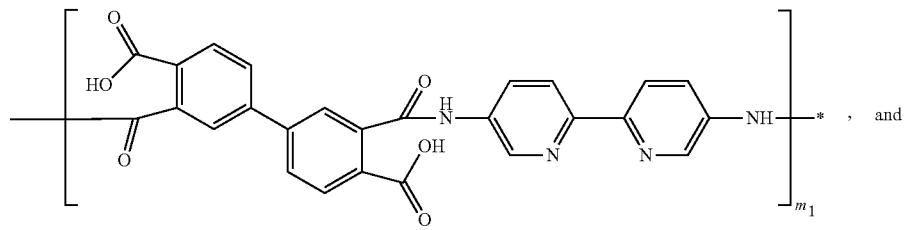
, and
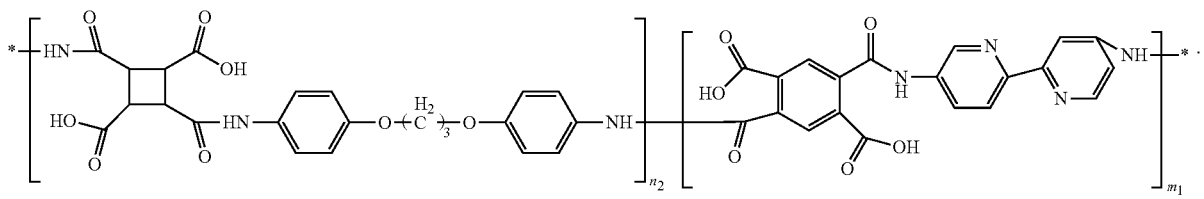

The disclosure further provides the display panel, including: a first substrate and a second substrate disposed opposite to each other, and a liquid crystal layer disposed between the first substrate and the second substrate;
the display panel further includes a first alignment film disposed on a side of the first substrate facing the liquid crystal layer and/or a second alignment film disposed on a side of the second substrate facing the liquid crystal layer;
wherein at least one of the first alignment film and the second alignment film includes the above-mentioned polymer.

By providing the organic compound applied to alignment films, the organic compound of the disclosure contains pyridine, therefore, conjugation of the alignment films can be improved, adsorption rates of ions on the alignment films can be reduced, and charge release speeds of the alignment films can be improved, so as to improve residual shadow of display panels applying the alignment films, thus improving quality of the display panels.

BRIEF DESCRIPTION OF THE DRAWINGS

In order to illustrate technical solutions in embodiments of the disclosure more clearly, the following briefly introduces drawings needed to be used in description of the embodiments. Obviously, the drawings in the following description are only some embodiments of the disclosure. For those skilled in the art, other drawings can be obtained from these drawings without paying creative effort.

DETAILED DESCRIPTION OF THE EMBODIMENT

Figure 1:
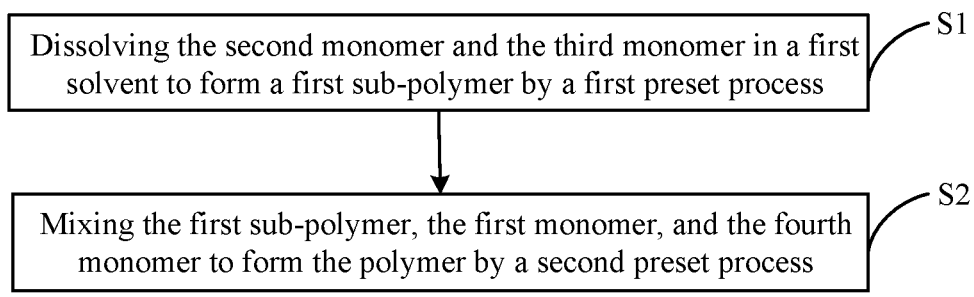
FIG. 1 is a schematic flow diagram of a preparation method of a polymer provided by an embodiment of the disclosure.

Technical solutions in the disclosure will be illustrated clearly and completely below in combination with drawings in the embodiments of the disclosure. Apparently, the described embodiments are only a part of the embodiments of the disclosure, not all of them. Based on the embodiments in the disclosure, all other embodiments obtained by those skilled in the art without paying creative effort belong to a scope of the disclosure. In addition, it should be understood that specific embodiments described herein are only used to explain the disclosure, not to limit the disclosure. In the disclosure, terms described herein for locations/directions, such as "up" and "down", generally refer to up and down in actual use or working state of devices, in particular drawing directions in the drawings, unless otherwise described. Terms such as "inside" and "outside" relate to outlines of the devices. In the disclosure, "optional" and "optionally" refer to present or absent of the element to which it refers. Each "optional" is independent, if there are multiple "optional" in a technical scheme, and there is no special description, contradiction, or mutual restriction. In the disclosure, technical features described in open forms include both closed technical solutions composed of listed features and open technical solutions containing listed features.

In the disclosure, an aromatic group, an aromatic ring, and an aromatic ring system have a same meaning and may be interchanged. "An aryl group or an aromatic group" refers to an aromatic hydrocarbon group derived from a basis of an aromatic ring compound removing an H. The aromatic ring compound may be a single ring aromatic group, a fused ring aromatic group, or a polycyclic aromatic group. For a polycyclic ring type, at least one ring is an aromatic ring system.

In the disclosure, a heteroaromatic group, a heteroaromatic ring, and a heteroaromatic ring system have a same meaning and may be interchanged. "A heteroaryl group or a heteroaromatic group" refers a basis of an aryl group with at least one carbon atom substituted by a non-carbon atom, and the non-carbon atom may be N, O, S, and the like.

In the disclosure, "substituted" means that one or more hydrogen atoms in one group are substituted by a substituent group. "Substituted or unsubstituted" means that a defined group may be substituted or not be substituted.

In the disclosure, a same substituent group at different substituent site may be independently selected from different groups. If a formula includes a plurality of Rs, each R can be independently selected from different groups.

In the disclosure, the "*" connected to a single bond indicates a binding site or a fused site.

In the disclosure, when a binding site of a group is not specified, it means that any of connectable sites in the group may be selected as the binding site.

In the present disclosure, when a fusing site of a group is not specified, it means that any of fusible sites in the group may be selected as the fusing site. Two or more adjacent sites in a group are preferably fusing sites.

In the present disclosure, "adjacent groups" means that there is no substitutable site between two substituent groups.

In related technologies, charges accumulated in alignment films are difficult to be released, which leads to residual shadow of display panels, thus making it difficult to improve quality of the display panels.

An embodiment of the disclosure provides an organic compound represented by formula (1) or formula (2):

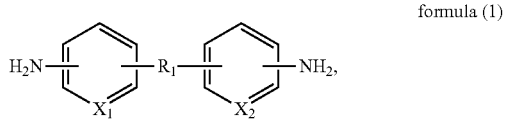

formula (1)

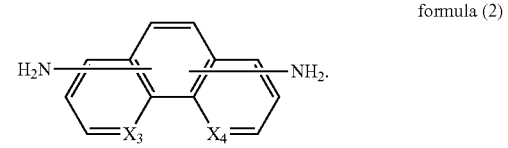

formula (2)

$X_1$, $X_2$, $X_3$, and $X_4$ are each independently selected from $CR_2$ and N, $X_1$ and $X_2$ are not $CR_2$ at the same time, and $X_3$ and $X_4$ are not $CR_2$ at the same time;
$R_1$ is independently selected from a single bond, a substituted or unsubstituted $C_6$-$C_{14}$ aromatic group, and a substituted or unsubstituted $C_5$-$C_{13}$ heteroaromatic group; and
$R_2$ is independently selected from —H or $NH_2$.

In the organic compound containing pyridine provided by the disclosure, nitrogen atom of the pyridine provides unshared electron pair, which improves conjugation of alignment films applying the organic compound, prevents from absorbing ions on surfaces of the alignment films, and improves a release rate of charges accumulated in the alignment films, resulting in improving residual shadow of display panels including the alignment films, thereby improving quality of the display panels.

In some embodiments, the organic compound is represented by formula (3) or formula (4):

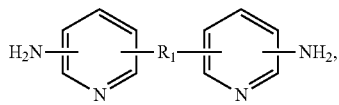

formula (3)

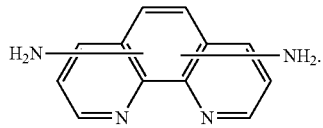

formula (4)

By increasing a quantity of pyridine in the organic compound, it is beneficial to further improve the conjugation of the alignment films applying the organic compound, prevent from absorbing the ions on the surfaces of the alignment films, and improve the release rate of the charges accumulated in the alignment films, thereby improving the residual shadow of the display panels including the alignment films, so as to improve the quality of the display panels.

In some embodiments, the organic compound is selected from following compounds:

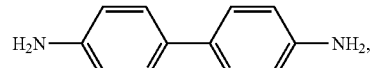

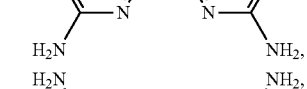

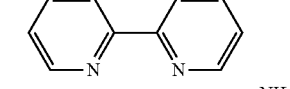

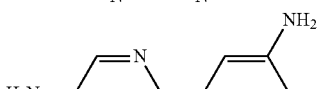

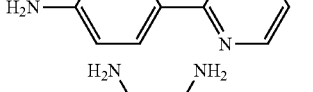

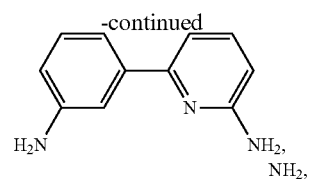

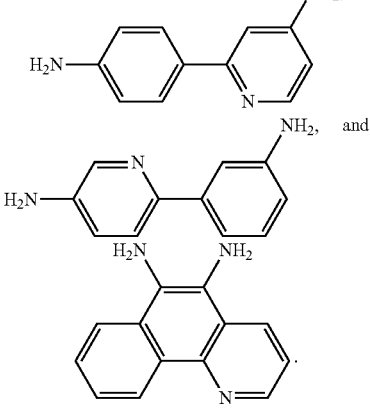

The organic compound is preferably selected from following compounds:

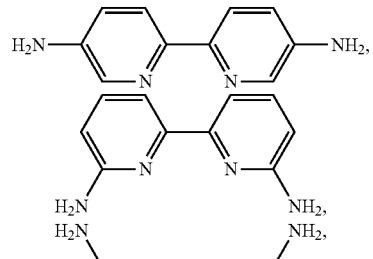

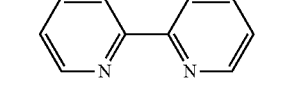

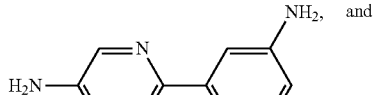

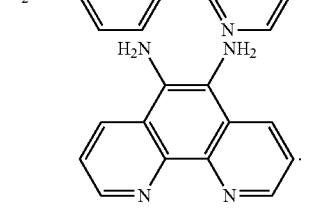

In the organic compound provided by the disclosure, nitrogen atom of the pyridine provides unshared electron pair, which improves the conjugation of the alignment films applying the organic compound, prevents from absorbing the ions on the surfaces of the alignment films, and improves the release rate of the charges accumulated in the alignment films, thereby improving the residual shadow of the display panels including the alignment films, thereby improving the quality of the display panels.

An embodiment of the disclosure further provides a polymer. The polymer is obtained by a reaction of a first type of raw material and a second type of raw material.

The first type of raw material includes the above-mentioned organic compound.

In some embodiments, the second type of raw material is polyacid or polyacid anhydride.

By using the above-mentioned organic compound in synthesis of the polymer, nitrogen atom of pyridine in the organic compound of the disclosure provides unshared electron pair, which improves the conjugation of the alignment films applying the organic compound, prevents from absorbing the ions on the surfaces of the alignment films, and improves the release rate of the charge accumulated in the alignment films, resulting in improving the residual shadow of the display panels containing the alignment films, thereby improving the quality of the display panels.

In some embodiments, the first type of raw material includes a first monomer and a second monomer. The first monomer is the above-mentioned organic compound. The second monomer is diamine. The second monomer the same or different from the first monomer.

In some embodiments, the second monomer is represented by

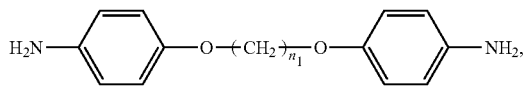 [SMILES: Nc1ccc(OCOc2ccc(N)cc2)cc1]

$n_1$ is an integer selected from 2, 3, and 4. When the polymer is applied in alignment films and the first monomer is the above-mentioned organic compound, it is easy for the first monomer to interact with liquid crystal molecules, thus facilitating formation of pre-tilt angles of the liquid crystal molecules.

In some embodiments, the second type of raw material includes a third monomer and a fourth monomer. The third monomer and the fourth monomer are tetracarboxylic dianhydride. The fourth monomer the same or different from the third monomer.

In some embodiments, the third monomer and the fourth monomer are selected from following compounds:

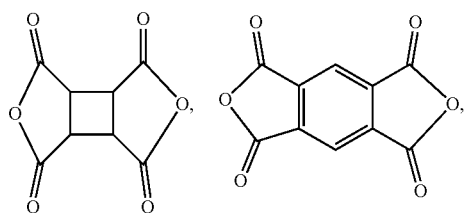

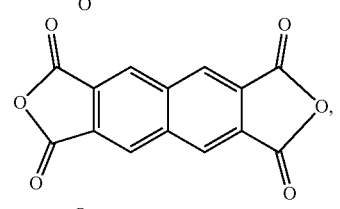

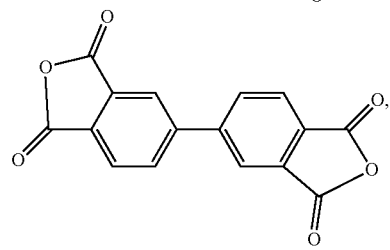

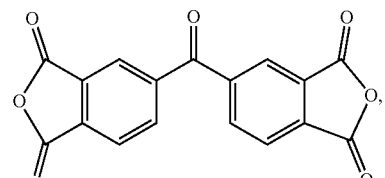

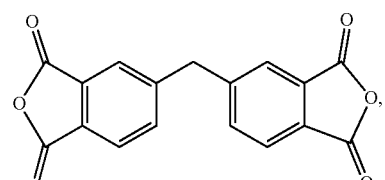

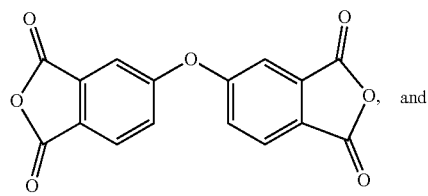

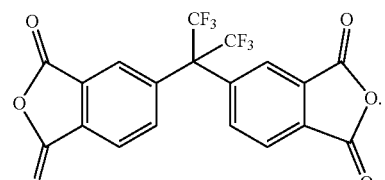

In some embodiments, the third monomer is preferably

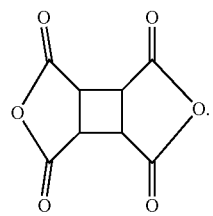 [SMILES: O=C1OC(=O)C2C1C1C(=O)OC(=O)C21]

In some embodiments, the fourth monomer is preferably selected from

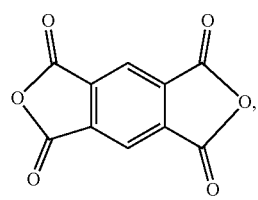

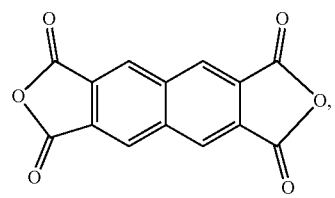

-continued

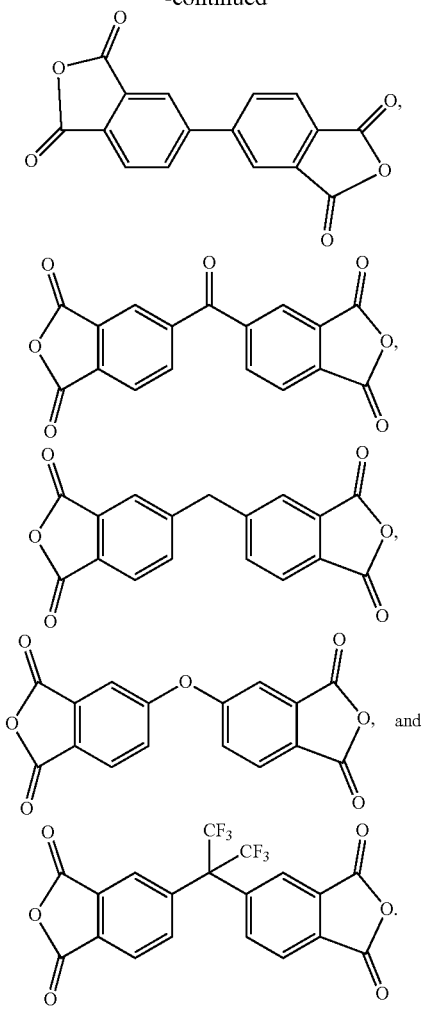

In some embodiments, the polymer is represented by formula (5):

formula (5)

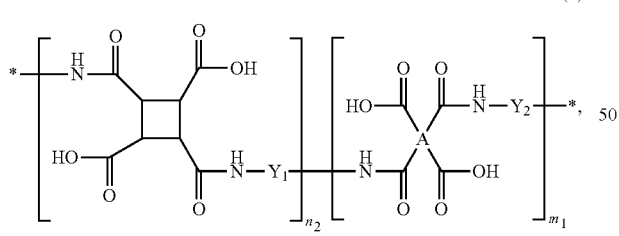

a ratio of $n_2$ to $m_1$ ranges from (2:8) to (5:5). For example, the ratio of $n_2$ to $m_1$ is 3:7, 4:6, etc.

$Y_1$ is represented by

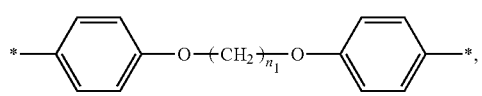

and $n_1$ is an integer selected from 2, 3, and 4.

A is selected from following compounds:

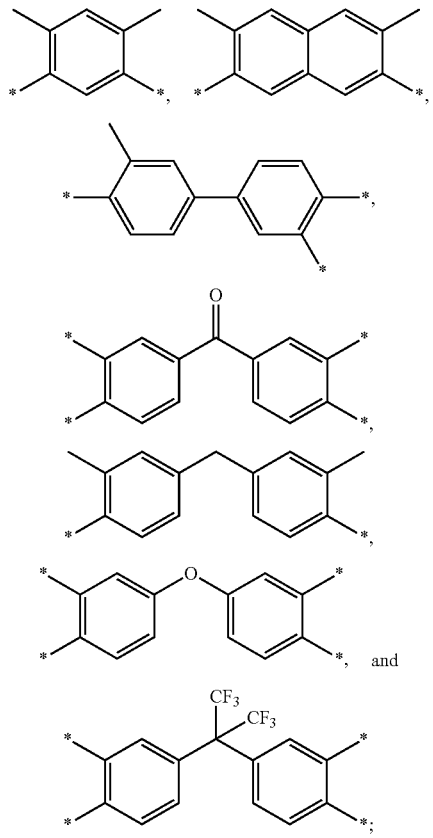

$Y_2$ is represented by formula (6) or formula (7):

formula (6)

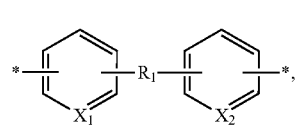

formula (7)

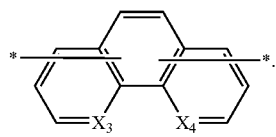

$X_1$, $X_2$, $X_3$, and $X_4$ are each independently selected from $CR_2$ and N, $X_1$ and $X_2$ are not $CR_2$ at the same time, and $X_3$ and $X_4$ are not $CR_2$ at the same time.

$R_1$ is independently selected from a single bond, a substituted or unsubstituted $C_6$-$C_{14}$ aromatic group, and a substituted or unsubstituted $C_5$-$C_{13}$ heteroaromatic group.

$R_2$ is independently selected from —H or $NH_2$.

Referring to FIG. 1, the disclosure also provides a preparation method of the polymer, including following steps.

Step S1: dissolving the second monomer and the third monomer in a first solvent to form a first sub-polymer by a first preset process.

In some embodiments, the second monomer is preferably

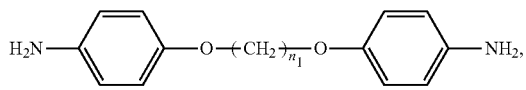

$n_1$ is an integer selected from 2, 3, and 4.

In some embodiments, the third monomer is preferably

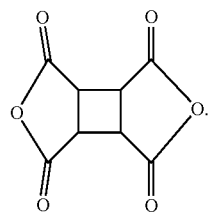

In some embodiments, the first solvent is N-methyl pyrrolidone.

In some embodiments, the step S1 includes step S11 and step S12.

The step S11: dissolving the third monomer in the first solvent, then dissolving the second monomer in the first solvent after injecting a first inert gas to the solution for a first gas loading time, then injecting the first inert gas to the solution for a second gas loading time, so as to obtain a first mixture.

In some embodiments, the first gas loading time is 30 minutes, the second gas loading time is 5 minutes, and the first inert gas is nitrogen.

The step S12: placing the first mixture in a closed container for a first reaction time to obtain a second mixture containing the first sub-polymer.

In some embodiments, the first reaction time is 6 hours.

In some embodiments, the first sub-polymer may be represented by

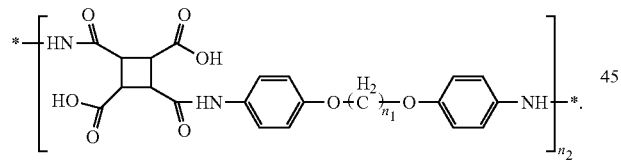

The step S2: mixing the first sub-polymer, the first monomer, and the fourth monomer to form the polymer by a second preset process.

In some embodiments, the first monomer is the above-mentioned organic compound.

In some embodiments, the fourth monomer is selected from following compounds:

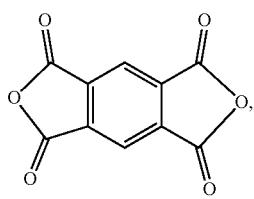

-continued

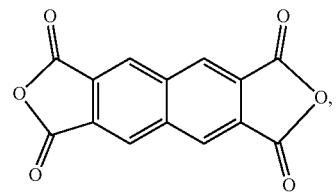

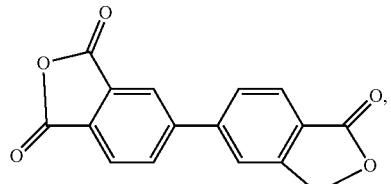

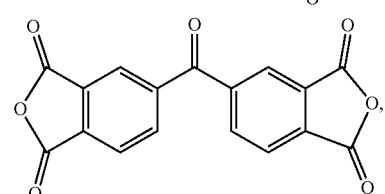

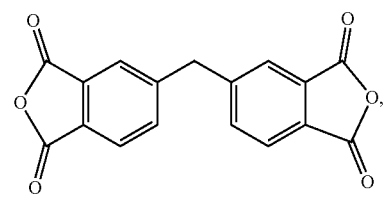

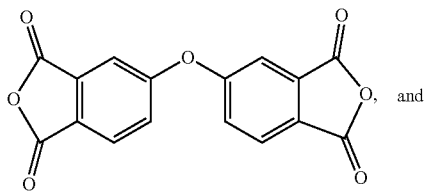

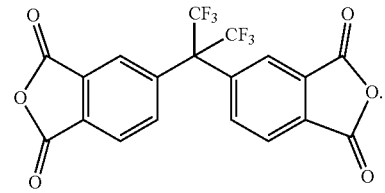

In some embodiments, the polymer is represented by formula (5):

formula (5)

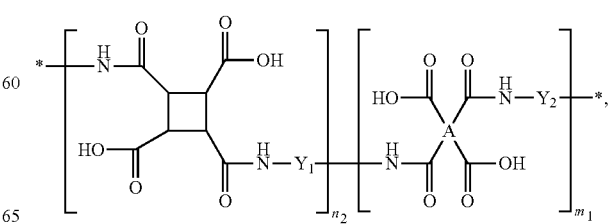

a ratio of $n_2$ to $m_1$ ranges from (2:8) to (5:5);
$Y_1$ is represented by

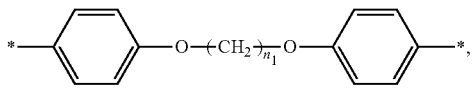

and $n_1$ is an integer selected from 2, 3, and 4;
A is selected from following compounds:

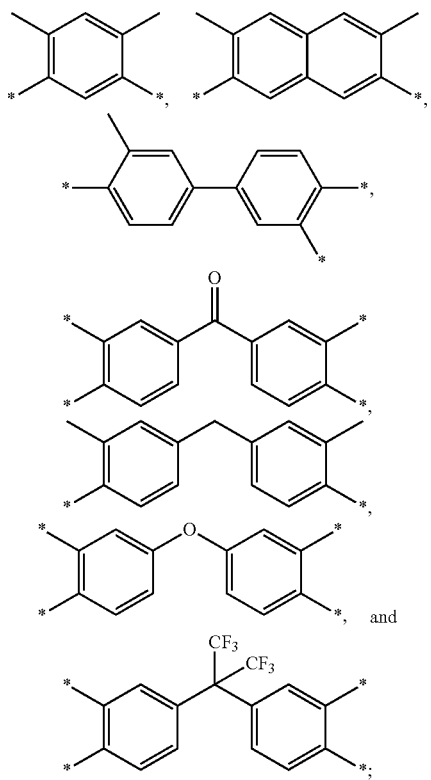

and
$Y_2$ is represented by formula (6) or formula (7):

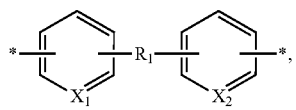

formula (6)

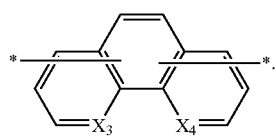

formula (7)

$X_1$, $X_2$, $X_3$, and $X_4$ are each independently selected from $CR_2$ and N, $X_1$ and $X_2$ are not $CR_2$ at the same time, and $X_3$ and $X_4$ are not $CR_2$ at the same time.

$R_1$ is independently selected from a single bond, a substituted or unsubstituted $C_6$-$C_{14}$ aromatic group, and a substituted or unsubstituted $C_5$-$C_{13}$ heteroaromatic group.

$R_2$ is independently selected from —H or $NH_2$.

In some embodiments, the step S2 includes step S21 and step S22.

The step S21: dissolving the fourth monomer in the second mixture, then dissolving the first monomer in the second mixture after injecting a second inert gas to the solution for a third gas loading time, so as to obtain a third mixture.

In some embodiments, the third gas loading time is 5 minutes, and the second inert gas is nitrogen.

The step S22: placing the third mixture in a closed container for a second reaction time to obtain the polymer.

In some embodiments, the second reaction time is 6 hours.

Exemplary preparation methods of the polymer provided by the disclosure are shown in the following exemplary embodiment 1 and embodiment 2.

Example 1

Synthesis of Polymer P1

A structure of the polymer P1 is as following:

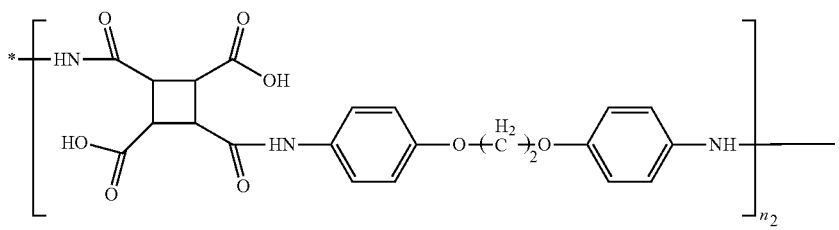

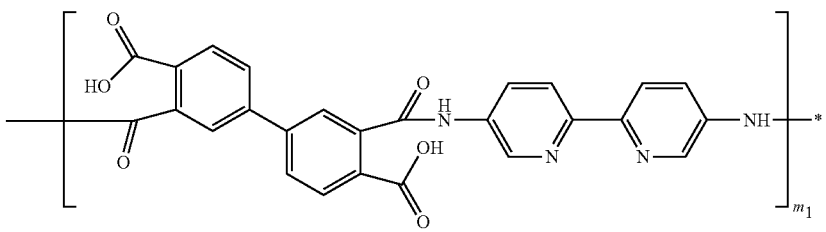

A synthetic route of the polymer P1 is as following:

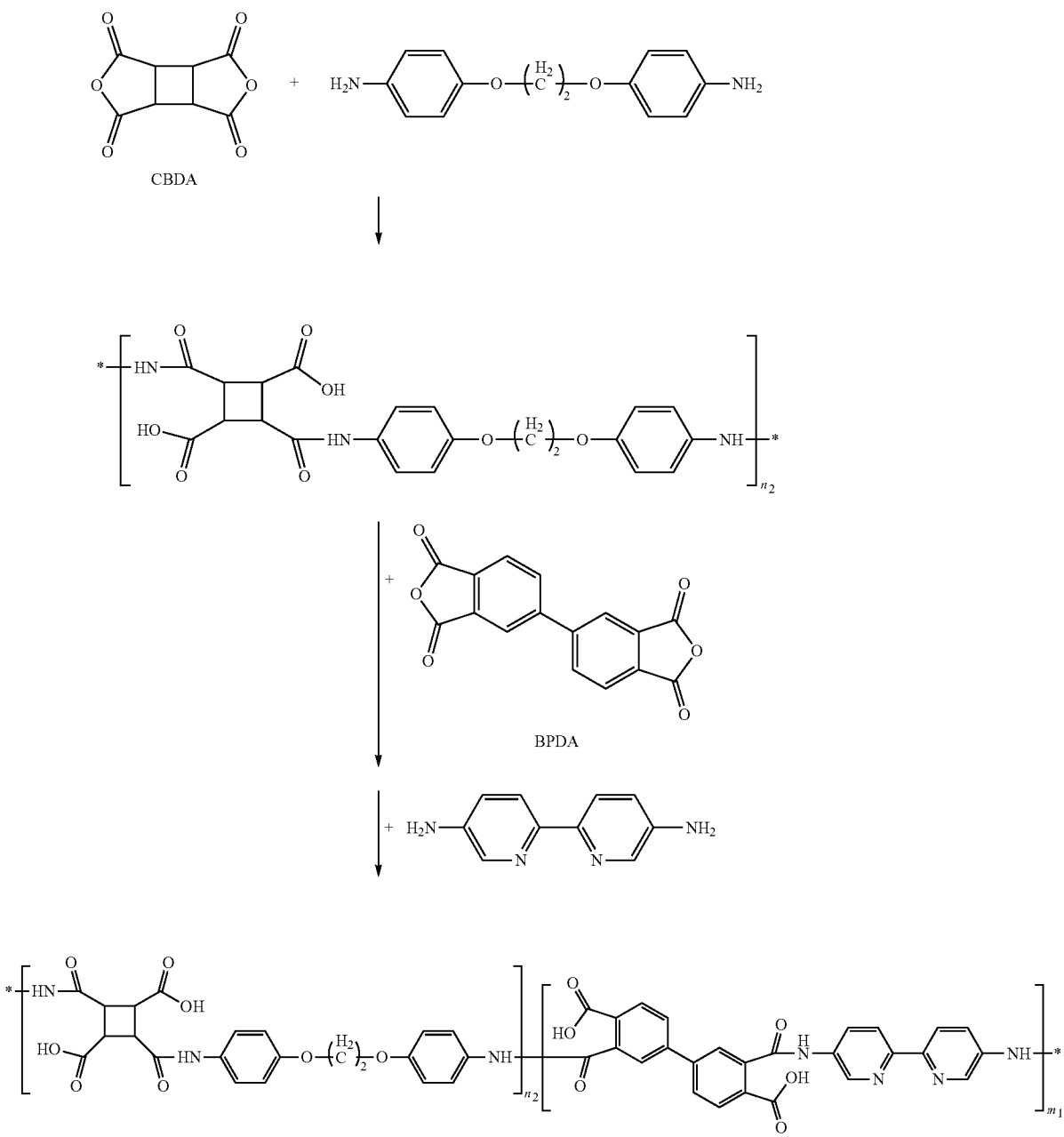

Synthesis steps of the polymer P1 are as following:

2.29 g (11.7 mmol) of 1,2,3,4-cyclobutanetetra-carboxylic acid dianhydride (CBDA) was dissolved in 50 g of N-methyl pyrrolidone (NMP), nitrogen was introduced to the solution for 30 minutes, then 2.69 g (11.7 mmol) of 1,2-bis (4-aminophenoxy) ethane was added to the solution, and nitrogen was continuously introduced to the solution for 5 minutes. Under a closed container, after the reaction was lasted for 6 hours, 6.11 g (20.8 mmol) of 3,3',4,4'-biphenyl tetracarboxylic diandhydride (BPDA) was added to the solution, and nitrogen was continuously introduced to the solution for 5 minutes. Then, 3.87 g of

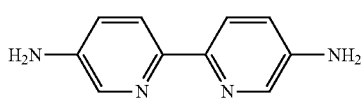

was added to the solution, and reacted for 6 hours under a closed container to obtain the polymer P1.

Example 2

Synthesis of Polymer P2

A structure of the polymer P2 is as following:

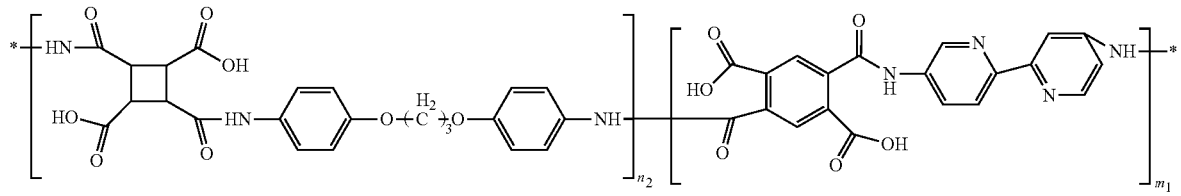

A synthetic route of the polymer P2 is as following:

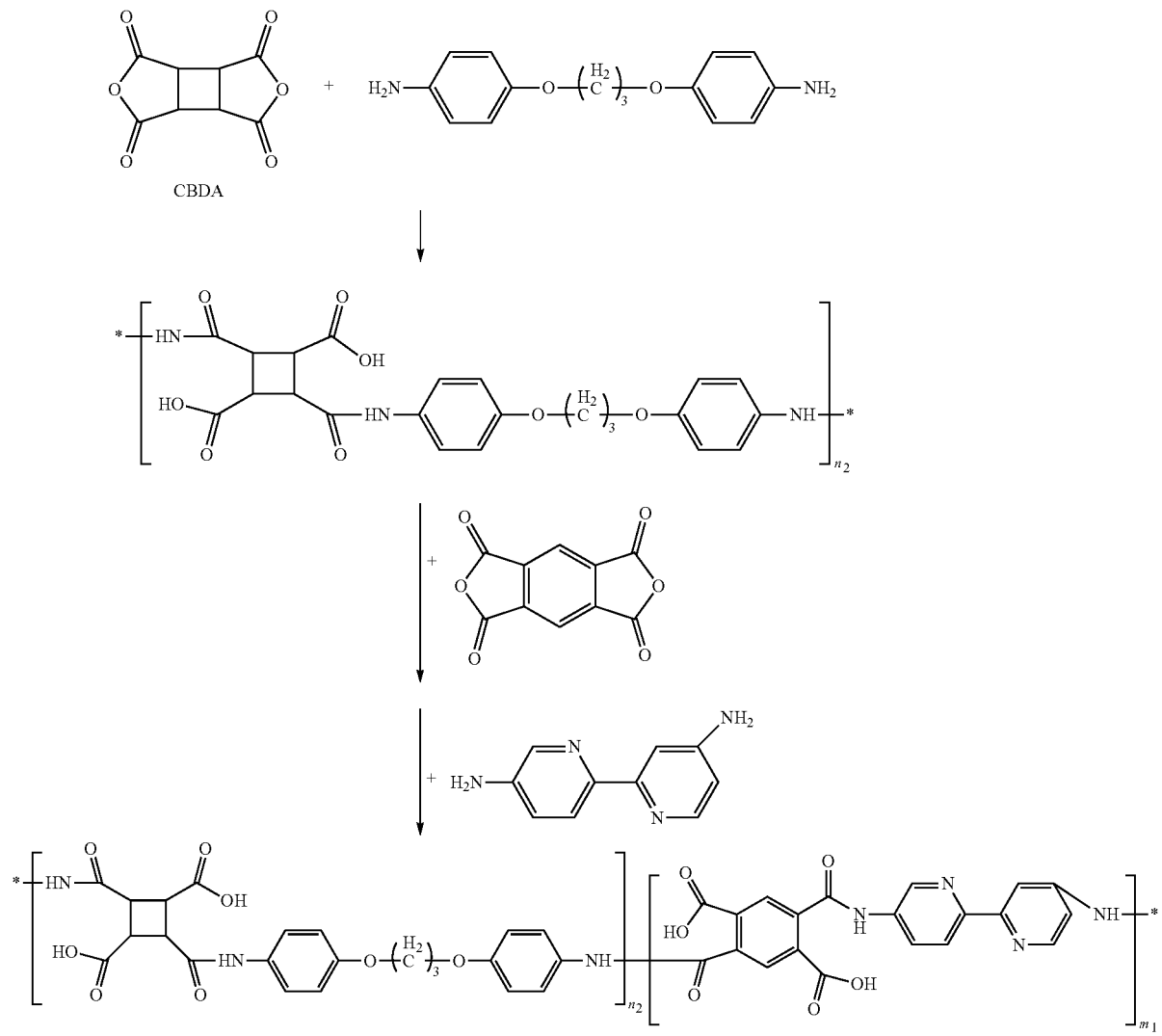

Synthesis steps of the polymer P2 are as following:

2.29 g (11.7 mmol) of CBDA was dissolved in 50 g of NMP, nitrogen was introduced to the solution for 30 minutes, then 3.022 g (11.7 mmol) of 4,4'-(1,3-propyloxy) diphenylamine was added to the solution, and nitrogen was continuously introduced to the solution for 5 minutes. Under a closed container, after the reaction was lasted for 6 hours, 4.537 g (20.8 mmol) of pyromellitic dianhydride was added to the solution, and nitrogen was continuously introduced to the solution for 5 minutes. Then, 3.87 g of

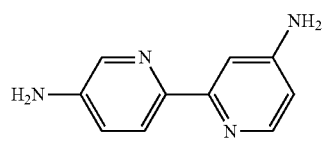

(CAS: 956479-26-8) was added to the solution, and reacted for 6 hours under a closed container to obtain the polymer P2.

Performance tests of alignment films formed by the polymer provided by the disclosure are shown in the following exemplary example 3, example 4, and comparative example 1.

Example 3

Manufacturing steps of a liquid crystal cell 1 include:

0.3 g of the polymer P1 was dissolved in 4 g of NMP and 1 g of ethylene glycol butyl methyl ether (BCS) to prepare an NMP/BCS solution including the polymer P1, the NMP/BCS solution was then coated on two indium tin oxide (ITO) substrates with an area of (2 cm*2 cm); then, the above-mentioned ITO substrates were baked at a temperature of 80° C. for 5 minutes, and baked at a temperature of 230° C. for 30 minutes, so as to obtain a first film layer with a thickness of 100 nm, respectively;

the above-mentioned ITO substrates were respectively irradiated with polarized ultraviolet light with irradiation energy of 100 mJ/cm$^2$ and a wavelength of 320 nm for 5 minutes to obtain a first alignment film, respectively;

a sealant was coated on a surface of one ITO substrate, then the one ITO substrate was paired with another ITO substrate; and liquid crystals were injected between the two ITO substrates under a vacuum atmosphere to obtain a horizontally aligned liquid crystal cell 1.

Example 4

Manufacturing steps of a liquid crystal cell 2 include:

0.3 g of the polymer P2 was dissolved in 4 g of NMP and 1 g of ethylene glycol butyl methyl ether (BCS) to prepare an NMP/BCS solution including the polymer P2, the NMP/BCS solution was then coated on two indium tin oxide (ITO) substrates with an area of (2 cm*2 cm); then, the above-mentioned ITO substrates were baked at a temperature of 80° C. for 5 minutes, and baked at a temperature of 230° C. for 30 minutes, so as to obtain a second film layer with a thickness of 100 nm, respectively;

the above-mentioned ITO substrates were respectively irradiated with polarized ultraviolet light with irradiation energy of 100 mJ/cm$^2$ and a wavelength of 320 nm for 5 minutes to obtain a second alignment film, respectively;

a sealant was coated on a surface of one ITO substrate, then the one ITO substrate was paired with another ITO substrate; and liquid crystals were injected between the two ITO substrates under a vacuum atmosphere to obtain a horizontally aligned liquid crystal cell 2.

Comparative Example 1

Manufacturing steps of a liquid crystal cell 3 include:

0.3 g of the polymer P3 was dissolved in 4 g of NMP and 1 g of ethylene glycol butyl methyl ether (BCS) to prepare an NMP/BCS solution including the polymer P3, the NMP/BCS solution was then coated on two indium tin oxide (ITO) substrates with an area of (2 cm*2 cm); then, the above-mentioned ITO substrates were baked at a temperature of 80° C. for 5 minutes, and baked at a temperature of 230° C. for 30 minutes, so as to obtain a third film layer with a thickness of 100 nm, respectively;

the above-mentioned ITO substrates were respectively irradiated with polarized ultraviolet light with irradiation energy of 100 mJ/cm$^2$ and a wavelength of 320 nm for 5 minutes to obtain a comparative alignment film, respectively;

a sealant was coated on a surface of one ITO substrate, then the one ITO substrate was paired with another ITO substrate; and liquid crystals were injected between the two ITO substrates under a vacuum atmosphere to obtain a horizontally aligned liquid crystal cell 3.

A structure of the polymer P3 is as following:

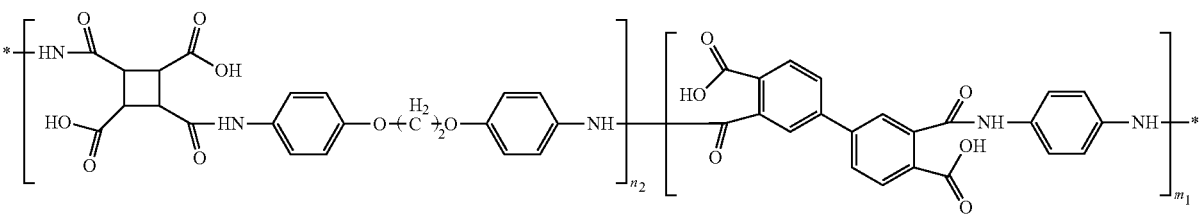

A synthetic route of the polymer P3 is as following:

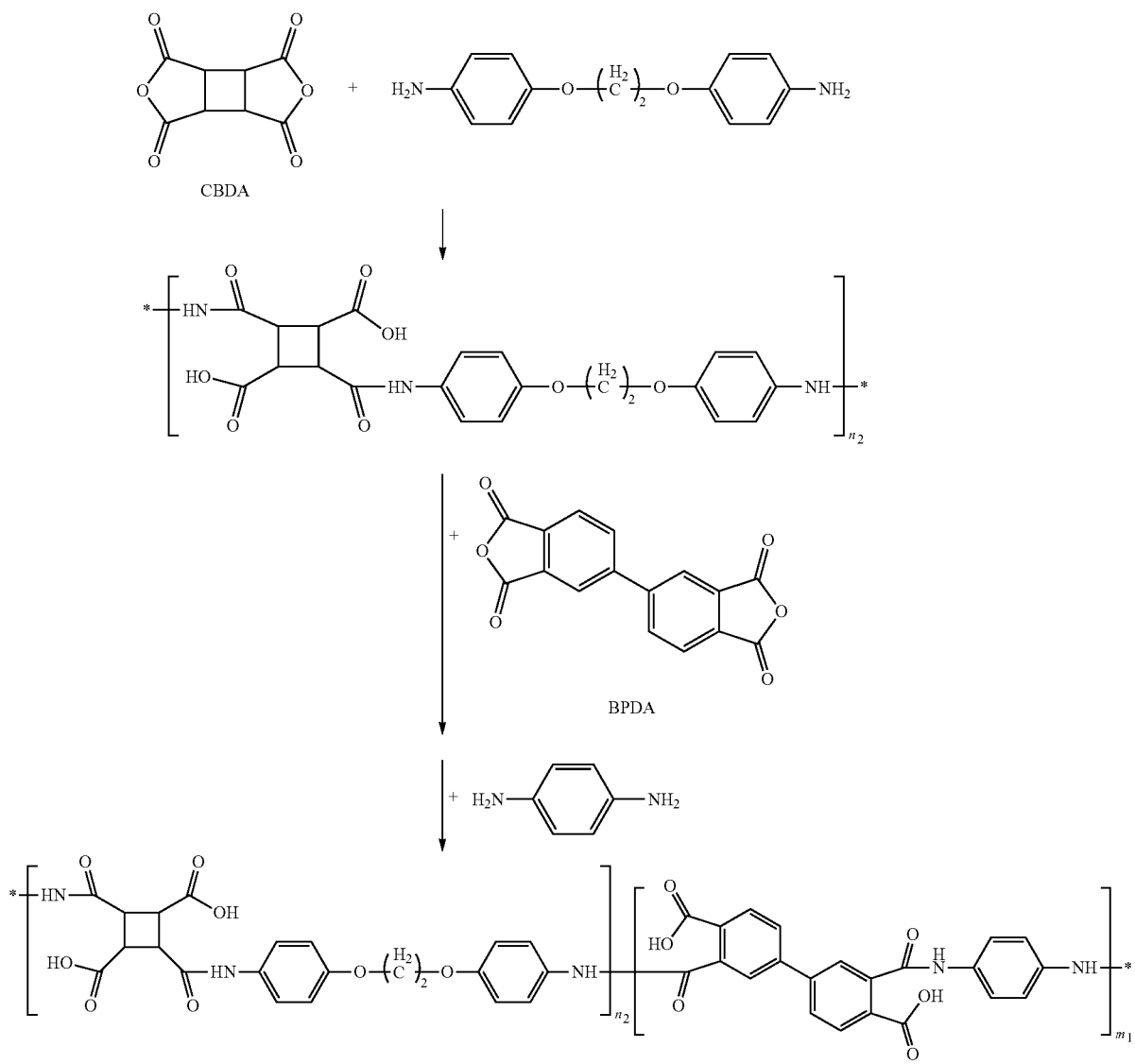

Synthesis steps of the polymer P3 are as following:

2.29 g (11.7 mmol) of CBDA was added in 50 g of NMP, nitrogen was introduced to the solution for 30 minutes, then 2.69 g (11.7 mmol) of 1,2-bis (4-aminophenoxy) ethane was added to the solution, and nitrogen was continuously introduced to the solution for 5 minutes. Under a closed container, after the reaction was lasted for 6 hours, 6.11 g (20.8 mmol) of BPDA was added to the solution, and nitrogen was continuously introduced to the solution for 5 minutes. Then, 2.249 g of p-phenylenediamine was added to the solution, and reacted for 6 hours under a closed container to obtain the polymer P3.

Residual Shadow Test

8 V of AC current was applied on the liquid crystal cell 1 to the liquid crystal cell 3 respectively, so as to light four points on each of the liquid crystal cell 1 to the liquid crystal cell 3 for 24 hours; and Instead of 8 V of AC current, 5 V of AC current was applied on the liquid crystal cell 1 to the liquid crystal cell 3, and other than four points lit on the liquid crystal cell 1 to the liquid crystal cell 3 respectively, another five points were lit on the liquid crystal cell 1 to the liquid crystal cell 3 respectively, then observing whether there is residual shadow.

Observed results: the liquid crystal cell 1 and the liquid crystal cell 2 have no residual shadow, and the liquid crystal cell 3 has residual shadow, indicating that the polymers provided by the examples of the disclosure have an effect of improving residual shadow of the display panels containing the alignment films containing the polymer, so as to improve quality of the display panels.

Residual DC Voltage (RDC) Test

5 V of DC current was applied on the liquid crystal cell 1 to the liquid crystal cell 3 for 5 minutes respectively; and the applied DC current was removed from the liquid crystal cell 1 to the liquid crystal cell 3; the results of voltage change with time from the liquid crystal cell 1 to the liquid crystal cell 3 were monitored after the applied DC current was removed.

Figure 2:
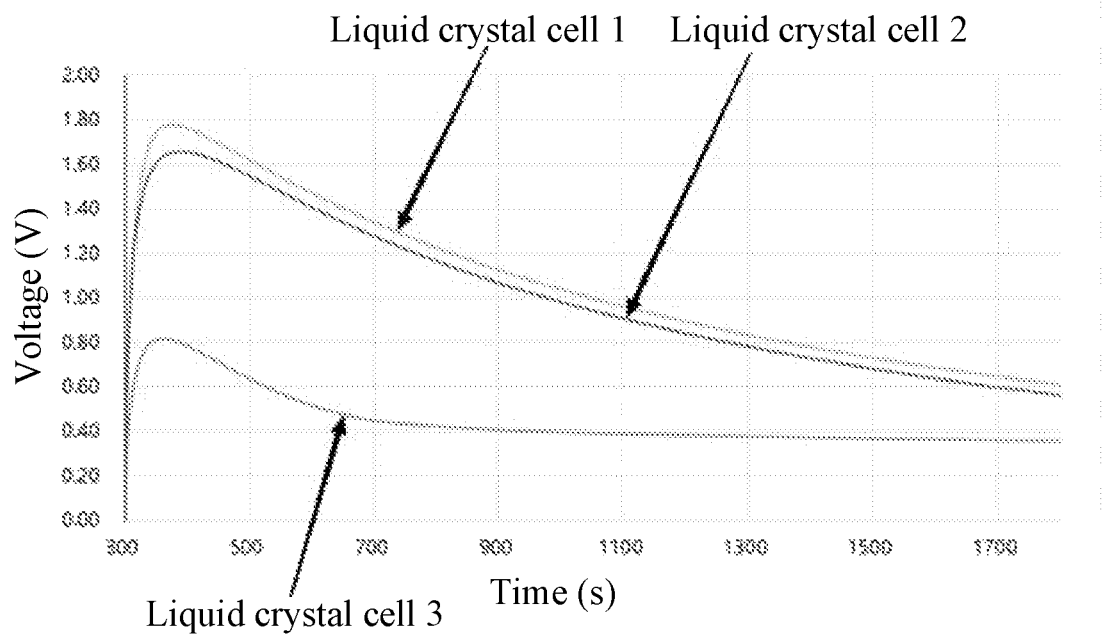
FIG. 2 is a residual DC voltage (RDC) diagram of liquid crystal cells provided by examples of the disclosure.

Referring to FIG. 2, in the RDC test results, voltages of the liquid crystal cell 1 to the liquid crystal cell 3 all increased first and then decreased with increase of time after removing the applied DC current, indicating that in the liquid crystal cell 1 to the liquid crystal cell 3, ions in alignment films located on two sides of the liquid crystal cell accumulates first and then release. Slope rates of curves obtained by changing voltages of the liquid crystal cell 1 and the liquid crystal cell 2 with time after their internal voltages reaching a peak value are greater than a slope rate of a curve obtained by changing voltages of the liquid crystal cell 3 with time after its internal voltage reaching a peak value, indicating that a release rate of ions in the alignment film of the liquid crystal cell 1 and a release rate of ions in the alignment film of the liquid crystal cell 2 are greater than a release rate of ions in the alignment film of the liquid crystal cell 3. That is, by using the polymer in forming alignment films in the examples of the disclosure, adsorption rates of ions on the alignment films can be reduced, thereby improving a release speed of charge accumulated in the alignment films, and improving residual shadow of the display panels applying the alignment films, thus improving the quality of the display panels.

Figure 3:
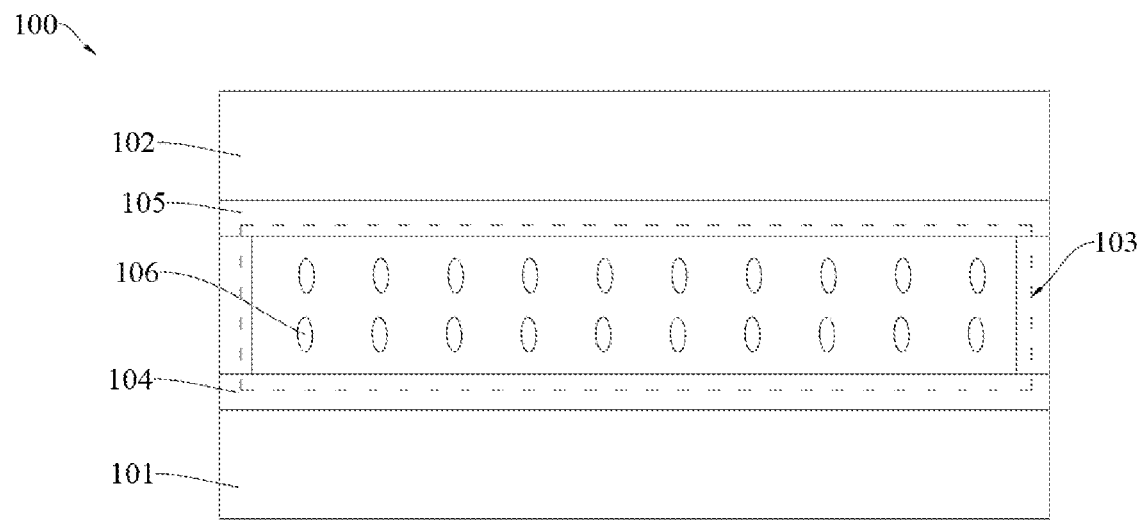
FIG. 3 is a schematic structural diagram of a display panel provided by an embodiment of the disclosure.

Referring to FIG. 3, an embodiment of the disclosure also provides a display panel 100. The display panel 100 includes a first substrate 101 and a second substrate 102 disposed opposite to each other, and a liquid crystal layer 103 disposed between the first substrate 101 and the second substrate 102.

The T display panel 100 also includes a first alignment film 104 disposed on a side of the first substrate 101 facing the liquid crystal layer 103 and/or a second alignment film 105 disposed on a side of the second substrate 102 facing the liquid crystal layer 103.

At least one of the first alignment film 104 and the second alignment film 105 includes the above-mentioned polymer.

In some embodiments, the liquid crystal layer 103 includes liquid crystal molecules 106.

In some embodiments, the display panel 100 also includes a frame glue disposed surrounding the liquid crystal layer 103. The frame glue is connected to the first substrate 101 and the second substrate 102, and the frame glue is configured to prevent invasion of external water and oxygen into the display panel.

In some embodiments, the first substrate 101 is an array substrate. The array substrate includes a first substrate, an active layer located on the first substrate, a first insulating layer located on the active layer, a gate insulating layer located on the first insulating layer, a second insulating layer located on the gate insulating layer, a source-drain layer located on the second insulating layer, and a third insulating layer located on the source-drain layer.

In some embodiments, the second substrate 102 is a color film substrate. The color film substrate includes a second substrate and a color film layer located on a side of the second substrate close to the liquid crystal layer. The color film layer includes black matrix, and a material of the black matrix may be a black organic photoresist material. A plurality of openings are defined in the black matrix to define a plurality of sub-pixel areas. A colored barrier layer is provided in the openings. The colored barrier layer includes any of a red sub-colored barrier layer, a green sub-colored barrier layer, and a blue sub-colored barrier layer. A material of the red sub-colored barrier layer may be a red organic photoresist material, a material of the green sub-colored barrier layer may be a green organic photoresist material, and a material of the blue sub-colored barrier layer may be a blue organic photoresist material.

In some embodiments, the display panel 100 also includes a pixel electrode and a common electrode opposite to the pixel electrode.

In some embodiments, the first substrate 101 includes the pixel electrode. The pixel electrode is located on the third insulating layer. The source-drain layer includes a source electrode and a drain electrode. The pixel electrode is electrically connected to the source electrode or the drain electrode.

In some embodiments, the second substrate 102 includes the common electrode. The common electrode is located on a side of the color film layer close to the liquid crystal layer.

In some embodiments, the first substrate 101 includes the common electrode. The common electrode is located on a side of the pixel electrode close to the liquid crystal layer, or the common electrode is located on a side of the pixel electrode with the pixel electrode.

In some embodiments, a material of the pixel electrode and a material of the common electrode are transparent conductive materials, such as indium tin oxide.

In some embodiments, a type of the display panel may be any of a twisted nematic (TN)-typed liquid crystal display panel, a super twisted nematic (STN)-typed liquid crystal display panel, an in plane switching (IPS)-typed liquid crystal display panel, and a fringe field switching (FFS)-typed liquid crystal display panel.

By using the polymer containing pyridine in forming the alignment films, nitrogen atom of pyridine of the disclosure provides unshared electron pair, which improves the conjugation of the alignment films, prevents from absorbing the ions on the surfaces of the alignment films, and improves the release rate of the charges accumulated in the alignment films, resulting in improving the residual shadow of the display panels including the alignment films, thereby improving the quality of the display panels.

Embodiments of the disclosure provide the organic compound, the polymer, and the display panel. The organic compound is represented by formula (1) or formula (2):

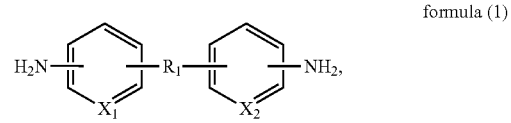

formula (1)

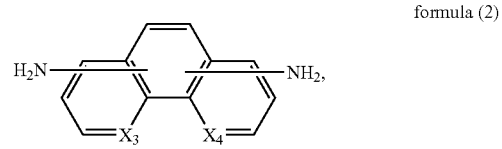

formula (2)

$X_1$, $X_2$, $X_3$, and $X_4$ are each independently selected from $CR_2$ and N, $X_1$ and $X_2$ are not $CR_2$ at the same time, and $X_3$ and $X_4$ are not $CR_2$ at the same time; $R_1$ is independently selected from a single bond, a substituted or unsubstituted $C_6$-$C_{14}$ aromatic group, and a substituted or unsubstituted $C_5$-$C_{13}$ heteroaromatic group; and $R_2$ is independently selected from —H or $NH_2$. By providing the organic compound applied to the alignment films, the organic compound of the disclosure contains pyridine, therefore, the conjugation of the alignment films can be improved, the adsorption rates of ions on the alignment films can be reduced, and the charge release speed of the alignment films can be improved, so as to improve residual shadow of display panels containing the alignment films, thereby improving quality of the display panels.

The organic compound, the polymer prepared by the organic compound, and the display panel containing the polymer provided by the embodiments of the disclosure are described in detail. In this paper, specific embodiments are adopted to illustrate a principle and implementation modes of the disclosure. The description of the above-mentioned embodiments is only used to help understand methods and a core idea of the disclosure. At the same time, for those skilled in the art, according to the idea of the disclosure, there will be changes in specific implementation modes and a scope of the disclosure. In conclusion, contents of the specification should not be interpreted as a limitation of the disclosure.

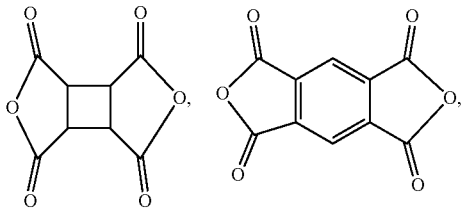

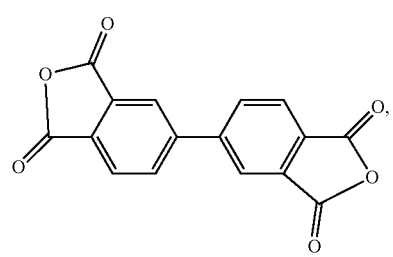

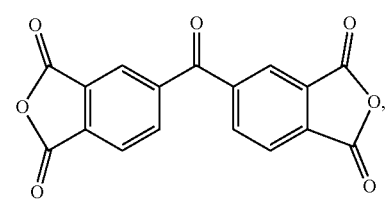

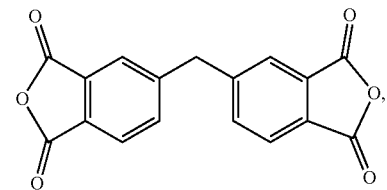

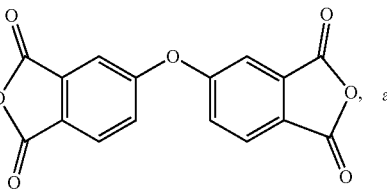

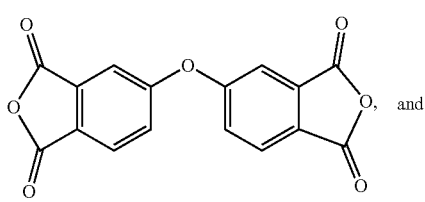

-continued
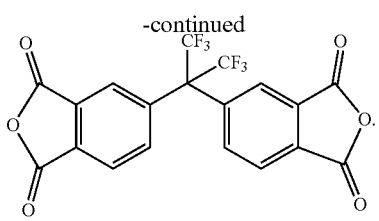
13. The polymer of claim 1, wherein the polymer is selected from the following compounds:
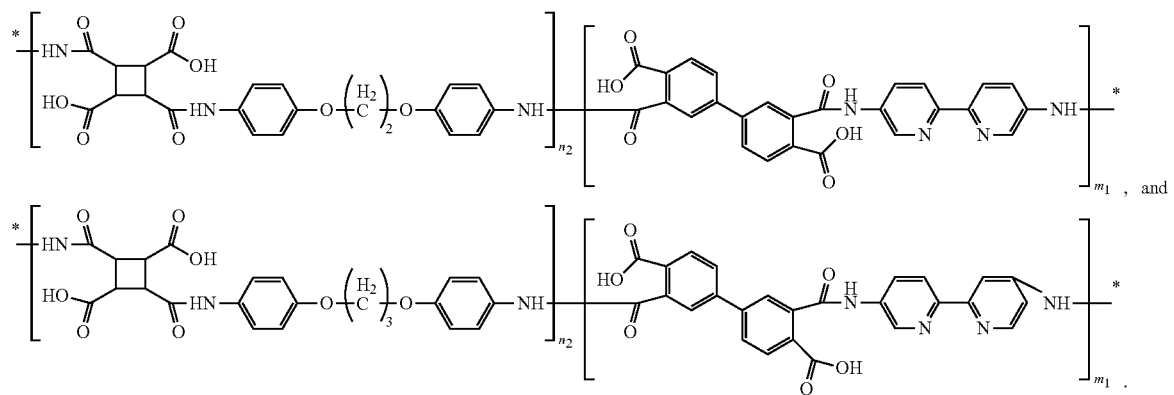

What is claimed is:

1. A polymer, wherein the polymer is obtained by a reaction of a first type of raw material and a second type of raw material;

wherein the first type of raw material comprises an organic compound represented by formula (1) or formula (2):

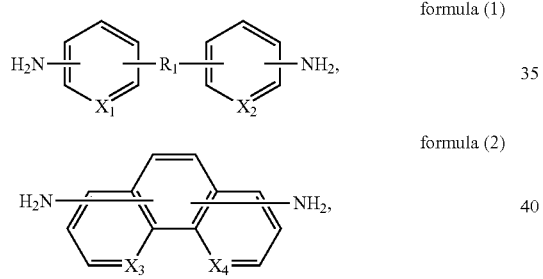

formula (1)

formula (2)

wherein $X_1$, $X_2$, $X_3$, and $X_4$ are each independently selected from $CR_2$ and N, $X_1$ and $X_2$ are not $CR_2$ at the same time, and $X_3$ and $X_4$ are not $CR_2$ at the same time;

$R_1$ is independently selected from a single bond, a substituted or unsubstituted $C_6$-$C_{14}$ aromatic group, or a substituted $C_5$-$C_{13}$ heteroaromatic group; and $R_2$ is independently selected from —H or $NH_2$;

wherein the polymer is represented by formula (5):

formula (5)

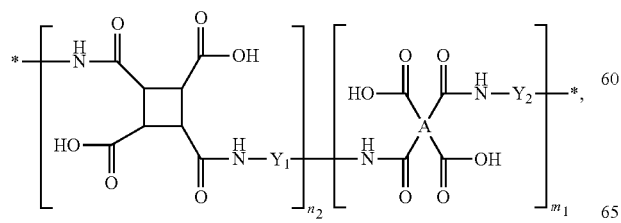

wherein a ratio of $n_2$ to $m_1$ ranges from (2:8) to (5:5); $Y_1$ is represented by

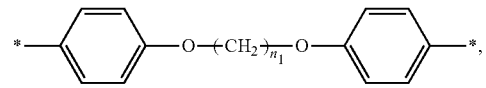

and $n_1$ is an integer selected from 2, 3, and 4;
A is selected from the following compounds:

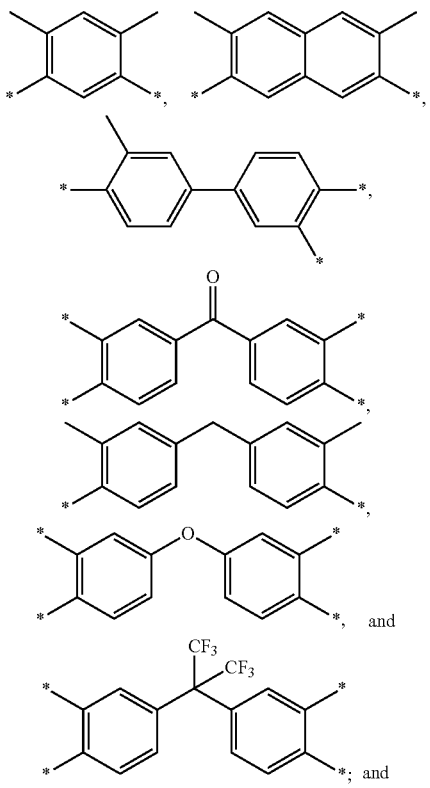

$Y_2$ is represented by formula (6) or formula (7);

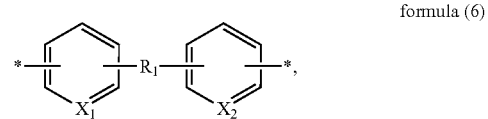

formula (6)

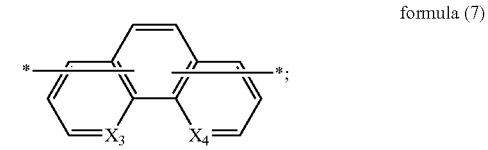

formula (7)

wherein in the formula (6) and the formula (7):
$X_1$, $X_2$, $X_3$, and $X_4$ are each independently selected from $CR_2$ and N, $X_1$ and $X_2$ are not $CR_2$ at the same time, and $X_3$ and $X_4$ are not $CR_2$ at the same time;
$R_1$ is independently selected from a single bond, a substituted or unsubstituted $C_6$-$C_{14}$ aromatic group, or a substituted $C_5$-$C_{13}$ heteroaromatic group; and
$R_2$ is independently selected from —H or $NH_2$.

2. The polymer of claim 1, wherein the second type of raw material is a polyacid or a polyacid anhydride.

3. The polymer of claim 1, wherein the first type of raw material comprises a first monomer and a second monomer, the first monomer is the organic compound, the second monomer is a diamine, and the second monomer is the same as or different from the first monomer; and the second type of raw material comprises a third monomer and a fourth monomer, the third monomer and the fourth monomer are tetracarboxylic dianhydrides, and the fourth monomer is the same as or different from the third monomer.

4. The polymer of claim 3, wherein the second monomer is represented by

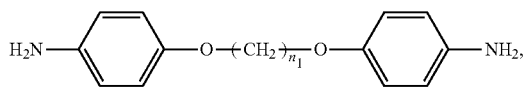

wherein $n_1$ is an integer selected from 2, 3, and 4.

5. The polymer of claim 3, wherein the third monomer and the fourth monomer are selected from the following compounds:

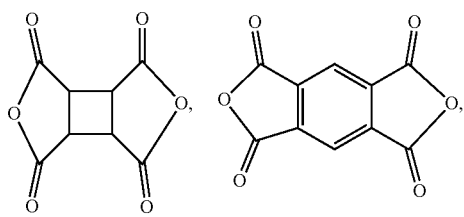

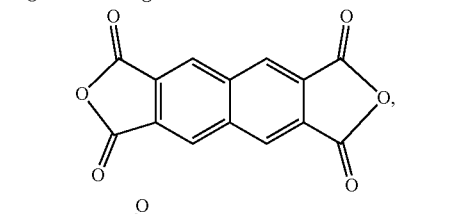

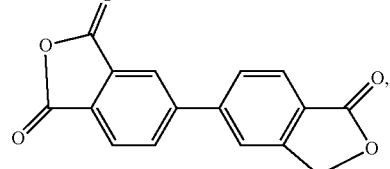

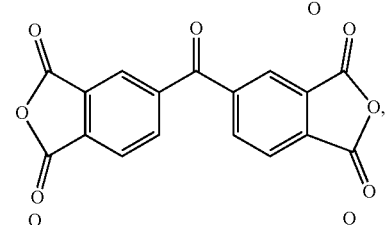

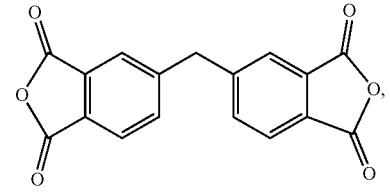

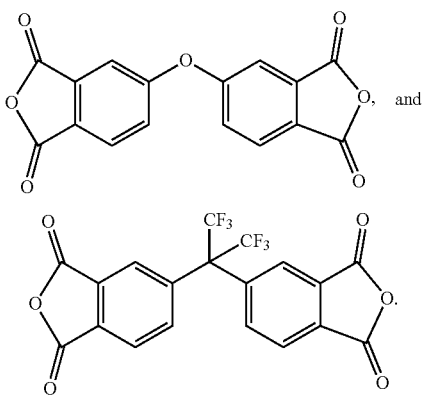

6. The polymer of claim 1, wherein the organic compound is represented by formula (3) or formula (4):

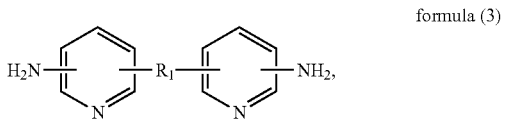
formula (3)

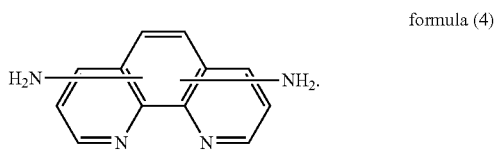
formula (4)

7. The polymer of claim 1, wherein the organic compound is selected from the following compounds:

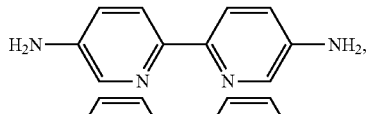

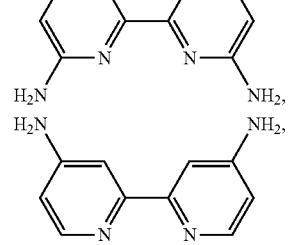

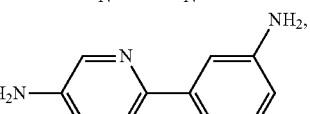

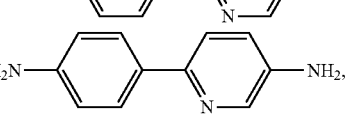

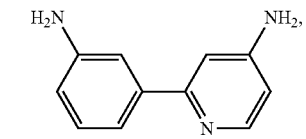

-continued

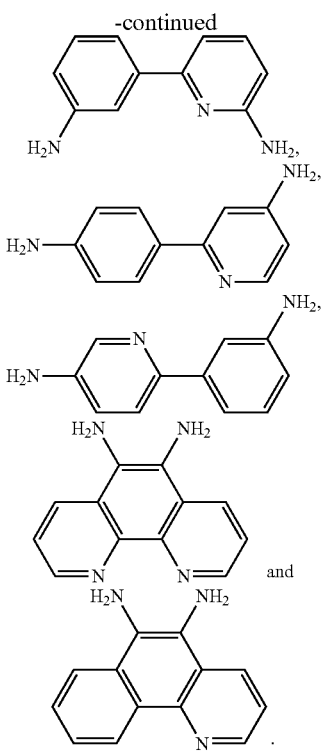

8. The polymer of claim 1, wherein the organic compound is selected from a following compound:

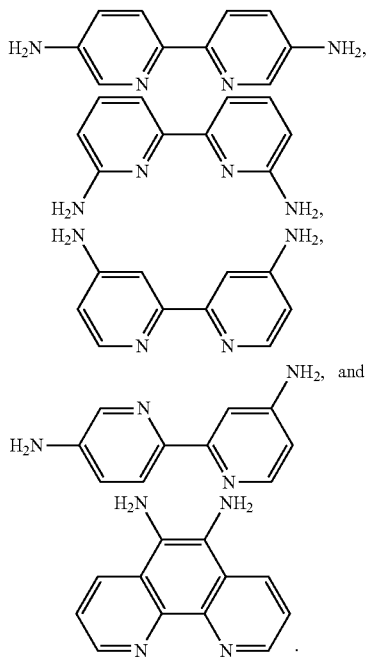

9. A display panel, wherein the display panel comprises a first substrate and a second substrate disposed opposite to each other, and a liquid crystal layer disposed between the first substrate and the second substrate;

the display panel further comprises a first alignment film disposed on a side of the first substrate facing the liquid crystal layer and/or a second alignment film disposed on a side of the second substrate facing the liquid crystal layer;

wherein at least one of the first alignment film and the second alignment film comprises a polymer obtained by a reaction of a first type of raw material and a second type of raw material;

wherein the first type of raw material comprises an organic compound represented by formula (1) or formula (2):

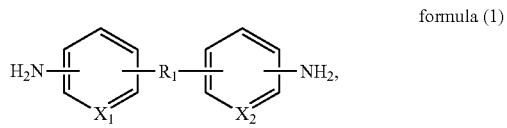

formula (1)

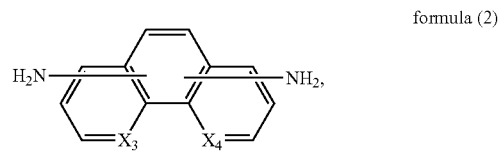

formula (2)

wherein $X_1$, $X_2$, $X_3$, and $X_4$ are each independently selected from $CR_2$ and N, $X_1$ and $X_2$ are not $CR_2$ at the same time, and $X_3$ and $X_4$ are not $CR_2$ at the same time;

$R_1$ is independently selected from a single bond, a substituted or unsubstituted $C_6$-$C_{14}$ aromatic group, or a substituted $C_5$-$C_{13}$ heteroaromatic group; and $R_2$ is independently selected from —H or $NH_2$;

wherein the polymer is represented by formula (5):

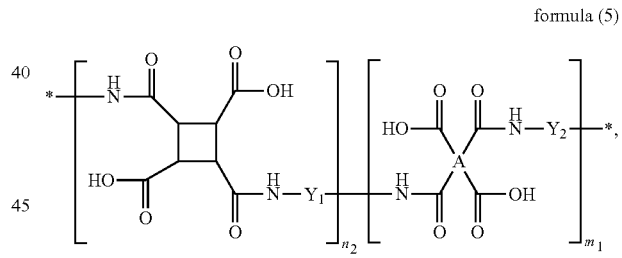

formula (5)

wherein a ratio of $n_2$ to $m_1$ ranges from (2:8) to (5:5);

$Y_1$ is represented by

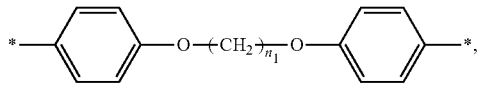

and $n_1$ is an integer selected from 2, 3, and 4;

A is selected from the following compounds:

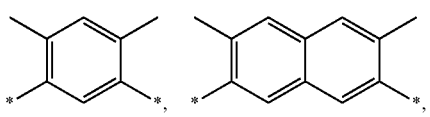

-continued

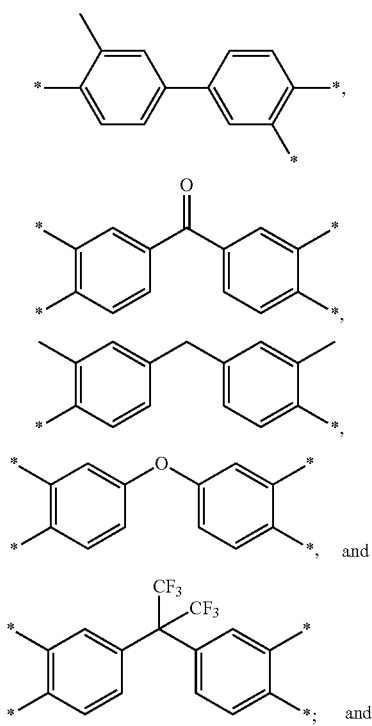

$Y_2$ is represented by formula (6) or formula (7):

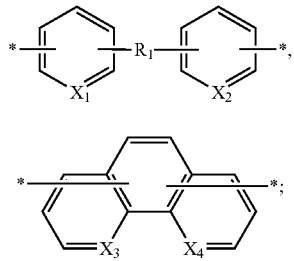

formula (6)

formula (7)

wherein in the formula (6) and the formula (7);

$X_1$, $X_2$, $X_3$, and $X_4$ are each independently selected from $CR_2$ and N, $X_1$ and $X_2$ are not $CR_2$ at the same time, and $X_3$ and $X_4$ are not $CR_2$ at the same time;

$R_1$ is independently selected from a single bond, a substituted or unsubstituted $C_6$-$C_{14}$ aromatic group, or a substituted $C_5$-$C_{13}$ heteroaromatic group; and $R_2$ is independently selected from —H or $NH_2$.

10. The display panel of claim 9, wherein the first type of raw material comprises a first monomer and a second monomer, the first monomer is the organic compound, the second monomer is a diamine, and the second monomer is the same as or different from the first monomer; and the second type of raw material comprises a third monomer and a fourth monomer, the third monomer and the fourth monomer are tetracarboxylic dianhydrides, and the fourth monomer is the same as or different from the third monomer.

11. The display panel of claim 10, wherein the second monomer is represented by

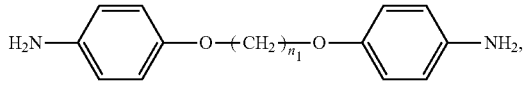

wherein $n_1$ is an integer selected from 2, 3, and 4.

12. The display panel of claim 10, wherein the third monomer and the fourth monomer are selected from the following compounds: